(12) United States Patent
Su et al.

(10) Patent No.: US 8,834,915 B2
(45) Date of Patent: Sep. 16, 2014

(54) DRUG-CONTAINING BIOABSORBABLE FIBERS AND IMPLANTS

(75) Inventors: Shih-Horng Su, Irvine, CA (US); Ting-Bin Yu, Irvine, CA (US); Minh Nguyen, Fountain Valley, CA (US)

(73) Assignee: Manli International Ltd., Singapore (SG)

( * ) Notice: Subject to any disclaimer, the term of this patent is extended or adjusted under 35 U.S.C. 154(b) by 0 days.

(21) Appl. No.: 13/435,487

(22) Filed: Mar. 30, 2012

(65) Prior Publication Data

US 2013/0256928 A1    Oct. 3, 2013

(51) Int. Cl.
*A61F 2/00*    (2006.01)

(52) U.S. Cl.
USPC ........................................................ 424/426

(58) Field of Classification Search
None
See application file for complete search history.

(56) References Cited

U.S. PATENT DOCUMENTS

| | | |
|---|---|---|
| 6,537,312 B2 | 3/2003 | Datta et al. |
| 2003/0040772 A1* | 2/2003 | Hyodoh et al. ............... 606/200 |
| 2007/0158880 A1 | 7/2007 | Dave |
| 2008/0166391 A1 | 7/2008 | Gibson et al. |
| 2008/0305144 A1 | 12/2008 | Brown et al. |
| 2009/0311304 A1 | 12/2009 | Borck et al. |
| 2010/0213634 A1 | 8/2010 | Headley et al. |
| 2011/0169197 A1 | 7/2011 | Huang et al. |
| 2011/0178594 A1 | 7/2011 | Kim et al. |

FOREIGN PATENT DOCUMENTS

| | | |
|---|---|---|
| EP | 0 604 022 A1 | 11/1993 |
| WO | WO 2010/017496 | 2/2011 |

OTHER PUBLICATIONS

Wielowieyska-Szybińska et al. Post Dermatol Alergol 2012, XXIX 2:118-122.*
The GI Cancer Institute: FAQ for cancer patients. Accessed online on Nov. 18, 2013 at gicancer.org.au/gi-cancer/faq-for-cancer-patients/.*
Max et al: "Paclitaxel/sirolimus combination coated drug-eluting stent: In vitro and in vivo drug release studies", Journal of Pharmaceutical and Biomedical Analysis, New York, NY US, vol. 54, No. 4, Mar. 25, 2011, pp. 807-811, XP027564561.
Shih-Horng Su et al., "Expandable Bioresorbable Endovascular Stent. I. Fabrication and Properties", Annals of Biomedical Engineering, vol. 31, pp. 667-677, 2003.
Meital Zilbermann et al., "Mechanical Properties and In Vitro Degradation of Bioresorbable Fibers and Expandable Fiber-Based Stents", Wiley *InterSience* pp. 792-799, 2005.
"Durin Biodegradable Implants", 2004, Durect Pharmaceutical Systems for Precise Delivery.

* cited by examiner

*Primary Examiner* — Carlos Azpuru
*Assistant Examiner* — Casey Hagopian
(74) *Attorney, Agent, or Firm* — Casari and McKenna, LLP

(57) ABSTRACT

Methods for producing drug-containing bioabsorbable fibers. Also disclosed are methods for treating diseases using a bioabsorbable drug delivery device.

7 Claims, No Drawings

DRUG-CONTAINING BIOABSORBABLE FIBERS AND IMPLANTS

BACKGROUND

Drug-containing polymeric fibers used for making stents are typically formed via co-compress molding, co-injection molding, or co-extrusion. For example, in a conventional co-extrusion process, one or more drug is compounded with a polymer resin. The compounded polymer resin is then melt extruded to form a fiber. However, the co-extrusion process has two important limitations. First, both compounding and melt extruding are carried out at the polymer's melting temperature, a temperature at which drugs are easily degraded. Second, the drug to polymer ratio must keep low in order to avoid breakage of the fiber during the melt extrusion process.

In fact, the drug to polymer ratio is critically important to the process of preparing drug-containing polymeric fibers by the above-mentioned techniques. It is routine in the art to keep the weight ratio of drug to polymer low so as to avoid severely compromising the mechanical strength of the polymeric fiber. Therefore, stents described in the prior art made using drug-containing polymeric fibers typically have a low drug content.

Polymer resins having a high- or ultra-high molecular weight are commonly used to make mechanically strong bioabsorbable polymeric fibers. Such strong fibers are desirable for use in manufacturing stents where mechanical strength is required. One drawback to using high molecular weight polymers is that the fibers made from them have a long degradation time. For example, a stent made from such fibers implanted in an artery will degrade slowly and may result in long term issues such as chronic foreign body reactions.

Another characteristic of existing drug-containing bioabsorbable fibers is a fixed drug release profile. Typically, upon implantation, a drug-delivery device formed from polymeric fibers initially releases a high concentration of drug that is rapidly reduced as the drug is released. In other words, the drug is present at a high concentration for only a short time. This drug release profile cannot be tailored to a specific disease condition.

There is a need to develop methods for producing drug-containing bioabsorbable polymeric fibers that overcome the problems associated with existing methods, e.g., low drug-loading capacity, manufacturing conditions that degrade the drug, long degradation time of the polymer, and non-programmable drug delivery profile.

SUMMARY

The main objective of the present invention is to provide methods for preparing drug-containing bioabsorbable fibers having both high strength and high drug content. Such fibers can be used in the manufacture of implantable, bioabsorbable drug delivery devices for treating various diseases. Another objective is to provide a method for treating diseases that result from cell over-proliferation.

Thus, one aspect of this invention relates to a method of preparing a drug-containing bioabsorbable fiber. The method includes a step in which a bioabsorbable polymer is dissolved in an organic solvent together with a drug. The resulting solution is dispensed into a mold, after which the organic solvent is removed by evaporation. The resulting fiber precursor is then drawn through a wire die to form a drug-containing bioabsorbable fiber having a uniform diameter. The entire method is carried out at a temperature between 5° C. and 80° C. so as not to degrade, damage, or otherwise destroy the drug.

Another aspect of this invention relates to a method of preparing a drug-containing bioabsorbable fiber that can have multiple layers, each of which can be loaded with a different drug. In this method, a drug-containing sheet is formed by dissolving a bioabsorbable polymer in an organic solvent together with a drug, dispensing the solution onto a flat surface, evaporating the organic solvent, and forming the drug-containing sheet into a fiber. The drug-containing sheet can have a second drug applied to it prior to forming the fiber, resulting in a fiber that contains two drugs. Similar to the method described above, this method is performed at a temperature between 5° C. and 80° C. so as not to degrade, damage, or otherwise destroy the drug.

Also provided is a method of treating a disease caused by cell over-proliferation. The method includes a step in which a bioabsorbable drug delivery device constructed of multi-layered drug-containing fibers is implanted at or near the site of the over-proliferating cells. The drug delivery device can release one or more drugs. When releasing more than one drug, each drug can be released from the implanted drug delivery device at a different time and a different rate.

The details of one or more embodiments of the invention are set forth in the description below. Other features, objects, and advantages of the invention will be apparent from the description and from the claims.

DETAILED DESCRIPTION

This invention is based on the need for bioabsorbable drug delivery devices that are both mechanically strong, yet are still degraded over an acceptable period of time. Additionally, a method is needed to produce drug-containing bioabsorbable fibers for use in constructing such drug delivery devices that allows for high drug loading without destroying the drug during the manufacturing process. The ultimate goal of this invention is to treat local and systemic diseases. To achieve that end, a drug delivery device should carry a high drug dosage, should be capable of loading multiple drugs, should have a controllable degradation rate and should have a multi-phase drug elution profile.

Accordingly, the present invention features methods for preparing a drug-containing bioabsorbable fiber.

In one method, a bioabsorbable polymer and one or more drugs are dissolved in an organic solvent, such as chloroform, methylene chloride, acetone, or tetrahydrofuran, to form a solution. The drug to polymer ratio ranges from 0.1:99.9 to 99.9:0.1 (wt:wt). For example, the drug to polymer ratio can be 70:30 or 10:90. The solution thus obtained is then dispensed into a channel of a fiber-shaped mold. The mold can be made of polytetrafluoroethylene (TEFLON™). The channel diameter ranges from 0.254 to 2.54 mm. The polymer/drug solution is preferably dispensed at a rate of from 0.02 to 200 µl/sec. Following this dispensing step, the organic solvent is then evaporated with or without applying a vacuum, preferably at room temperature, to yield a drug-containing fiber precursor. If desired, the channel can be filled in stages. This allows for inclusion of different polymer/drug mixtures within the same fiber. The fiber precursor is then drawn through a die in order to create a drug-containing fiber having a uniform diameter. This diameter can be 0.025 to 0.80 mm. The temperature of the die can be the same as the glass transition temperature of the polymer used for making the fiber. The steps of this method are carried out at a temperature of 5° C. to 80° C. For example, the dispensing step or the evaporating step can be carried out at a temperature of 5° C. to 40° C.

In a second method, a bioabsorbable polymer and one or more drugs are dissolved in an organic solvent, such as chloroform, methylene chloride, acetone, or tetrahydrofuran, to form a solution. The solution thus obtained is then dispensed onto a flat surface, after which the organic solvent is evaporated with or without applying a vacuum, preferably at room temperature. This results in formation of a sheet of drug-containing bioabsorbable polymer. Two edges of the sheet are joined together to form a drug-containing bioabsorbable tube. The edges can be joined together using the organic solvent or a laser to melt the edges together. A second drug can be added to the sheet of drug-containing bioabsorbable polymer either before or after the edges are joined together. The second drug can be in solid or liquid form. The two ends of the tube are sealed such that the second drug remains contained inside the tube. The sealed tube is drawn through a die to form a drug-containing bioabsorbable fiber such that the drug-containing bioabsorbable fiber has a uniform diameter. The fiber diameter can be 0.025 to 0.80 mm. The temperature of the die can be the same as the glass transition temperature of the polymer used for making the fiber. Similar to the first method described above, this method is carried out at a temperature of 5° C. to 80° C. Also like the first method, the dispensing step or the evaporating step can be carried out at a temperature of 5° C. to 40° C.

In both methods described above, the bioabsorbable polymer can be polydioxanone, polyglycolide, polycaprolactone, polylactides, poly-L-lactide, poly-D,L-lactide, poly(L-lactide-co-glycolide), poly(D,L-lactide-co-glycolide), poly(L-lactide-co-D,L-lactide), poly(L-lactide-co-trimethylene carbonate), polyhydroxyvalerate, or ethylvinylacetate. One or more organic solvents can be used to dissolve one or more of the just-mentioned polymers prior to fiber formation.

A multi-layer fiber that contains any number of drugs can be made by combining the two methods described above. For example, a polymer sheet that contains drug A can be wrapped around a tube that contains drug B in the wall of the tube and drug C in the interior of the tube. Using the above methods, additional drug-containing polymer layers can be added if more drugs are required for a particular application.

As mentioned above, one drawback of using a fiber constructed of a high molecular weight polymer is its long degradation time. It is disclosed that additives such as weak acids, weak bases, or their anhydrates can be mixed with the polymer prior to fiber formation in order to increase the degradation rate of that fiber. Such additives serve as a catalyst to accelerate the polymer degradation rate.

The weight percentage of acid, base, or their anhydrates correlates with the degradation rate of a polymer. For example, a polymer film constructed of polycaprolactone that contains 2% by weight of a weak acid degraded faster than a film constructed from the same polymer in the absence of that acid. Increasing the acid content to 5% by weight further accelerated the degradation rate. Similarly, a polycaprolactone film that contains 2% or 5% by weight of a weak base also degraded faster than the base-free polymer film.

In another example, the average molecular weight of a poly-D,L-lactide fiber constructed using 3% lactic acid decreased by 66% following a 4-week incubation in phosphate-buffered saline (PBS). Increasing the amount of lactic acid used to 5% resulted in a 78% decrease in the polymer's average molecular weight over the same 4-week period. In contrast, the average molecular weight of a poly-D,L-lactide polymer in the absence of a weak acid dropped only 11% after 4 weeks of incubation in PBS.

Unexpectedly, a poly-D,L-lactide fiber made with 5% lactic acid having a diameter of 0.165 mm has a similar initial tensile strength as compared to a poly-D,L-lactide fiber made without lactic acid. More specifically, such a lactic acid-containing fiber has a maximum load before fiber break of 1.1 pounds force (lbf), as compared to a maximum load of 0.9 lbf for a similar fiber lacking the acid. In other words, a fast degrading fiber can be made using the above methods that is just as strong as a slow degrading fiber.

Whether a weak acid, a weak base, or their anhydrate is added to the polymer during fiber formation, the initial tensile strength of the fiber is not affected if the weight percentage of the additive is less than or equal to 5%.

Weak acids that can be used to increase the degradation rate of a polymeric fiber include but are not limited to formic acid, acetic acid, lactic acid, citric acid, oxalic acid, malic acid, pyruvic acid, succinic acid, citramalic acid, phosphoric acid aspartic acid, glutamic acid, a peptide containing aspartic acid and glutamic acid, mucic acid, tartaric acid, gluconic acid, acetylsalicylic acid, and their anhydrates. Mixtures of these acids can also be used.

Examples of weak bases that can be mixed with polymers to increase their degradation rate are ammonia, trimethyl ammonia, pyridine, ammonium hydroxide, sodium hydroxide, potassium hydroxide, sodium carbonate, potassium carbonate, sodium borate, trisodium phosphate, sodium silicate, potassium acetate, anhydrates of the above-listed bases, or mixtures thereof.

The criterion for selecting a weak acid or a weak base is drug compatibility. For example, doxorubicin is more stable in an acidic environment. To form a fiber that includes doxorubicin, lactic acid or lactide is added to the polymer for making the fiber. In a second example, paclitaxel has poor solubility and stability in an aqueous solution. It is most stable in an aqueous solution that has a pH range of 3-5. To form a paclitaxel-containing fiber, lactic acid/lactide or citric acid/citrate is added to the polymer for making the fiber. For base-sensitive agents, e.g., temozolomide and fluorouracil, a weak acid is added when forming a fiber. On the other hand, acid-sensitive agents such as asparaginase should be added with a weak base like sodium carbonate to form a fiber.

The polymeric fibers having high tensile strength described above can be used to construct a drug delivery device such as a stent. The mechanical strength of such a stent is high since it inherits the strength from the fiber. As mentioned above, the fiber can be hollow and can contain pure drug loaded in its center, yet the tensile strength of such a fiber can be as high as a solid fiber. This property boosts the weight percentage of drug content in a stent made from the fiber without compromising the mechanical strength of the stent.

Stents manufactured using the inventive fibers described above, as compared to prior art stents, have significantly higher drug loading, a controllable degradation rate, and high mechanical strength. These stents can treat both localized and systemic diseases (acute, sub-acute, or chronic) by adjusting the amount and the type of drug loadings.

Because of the programmable degradation rate, the drug release profile of this invention is also unique. For example, a solid fiber that contains a single drug can be used to create a drug delivery device, e.g., a stent, having a single-phase drug delivery profile. Single phase means the drug concentration released into the surrounding medium reaches a peak level only once during the span of drug release.

A unique multi-phased drug elution profile can be created by combining, in a single device, fibers containing layers that include different drugs where the layers degrade at different rates. By way of example, a hollow fiber containing drug 1 in the fiber wall can also contain drug 2 loaded in its center. When this fiber is exposed to a releasing medium, it immediately starts releasing drug 1. Soon the concentration of drug 1 reaches a peak level in the releasing medium and then begins to drop off. Drug 1 can be completely released before the fiber starts degrading. Once the fiber is degraded to a certain degree, drug 2 is released into the releasing medium. If drug 1 and 2 are the same, then the drug concentration in the releasing medium starts increasing until it reaches another peak. A skilled person in the art would appreciate that, in view of the above, a fiber can be designed and constructed to release any number of drugs in any order at predetermined rates.

A drug delivery device as described above can be implanted at or close to a disease site. Drugs released from the implant can treat the disease. The drug delivery device can advantageously be used to treat diseases that result from cell over-proliferation. Two such diseases are cancer and stenosis.

For anti-cancer indication, stents carry drugs including hormone therapy agents (abiraterone, aminoglutethimide, anastrozole, methyltestosterone, testosterone enanthenate, fluoxymesterone, bicalutamide, denosumab, degarelix, dolasetron, exemestane, flutamide, fulvestrant, goserelin, histrelin, letrozole, leuprolide, megestrol, mitotane, nilutamide, tamoxifen, testolactone, toremifene, triptorelin), immunotherapy agents (alemtuzumab, brentuximab vedotin, cetuximab, denileukin diftitox, ipilimumab, lenalidomide, ofatumumab, panitumumab, rituximab, thalidomide, tositumomab, trastuzumab, $^{90}$Y-ibritumomab tiuxetan), targeted therapy agents (alitretinoin, bexarotene, biolimus, crizotinib, dasatinib, erlotinib, everolimus, gefitinib, imatinib, lapatinib, nilotinib, pazopanib, pimecrolimus, sirolimus, sorafenib, sunitinib, tacrolimus, temsirolimus, vandetanib, vemurafenib, zotarolimus), chemotherapy agents (altretamine, asparaginase, azacitidine, bendamustine, bleomycin, brentuximab vedotin, busulfan, cabazitaxel, capecitabine, carboplatin, carmustine, chlorambucil, cisplatin, cytarabine, dacarbazine, dactinomycin, daunorubicin, docetaxel, doxorubicin, epirubicin, eribulin mesylate, erlotinib, estramustine, etoposide, floxuridine, fludarabine, fluorouracil, gemcitabine, hydroxyurea, idarubicin, ifosfamide, irinotecan, ixabepilone, lomustine, mechlorethamine, melphalan, mercaptopurine, methotrexate, mitoxantrone, mitomycin, nelarabine, oxaliplatin, paclitaxel, pemetrexed, pentostatin, pralatrexate, temozolomide, teniposide, thioguanine, thiotepa, topotecan, vinblastine, vincristine) and anti-cancer agents (arsenic trioxide, clofarabine, decitabine, pegaspargase, procarbazine, romidepsin, streptozocin, vorinostat). Any of the just-mentioned drugs can be loaded into the center, the wall, or both the center and the wall of the fiber used to form the drug delivery device.

A combination of drugs is often used to treat cancer. For example, a combination of sorafenib and sirolimus is used for treating hepatocellular carcinoma, everolimus and octreotide for treating neuroendocrine tumors, and cisplatin, paclitaxel, and epirubicin for treating ovarian cancer. To effect combination chemotherapy, a drug delivery device, e.g., a stent, can be manufactured using fibers loaded with two or more drugs. For example, one drug can be loaded in the tube wall, while a second drug is loaded in the center of the fiber.

A bioabsorbable drug delivery device that includes a multi-layered fiber loaded with more than one drug has additional advantages over existing devices for treating cancer. The device can release the different drugs at different times.

Cytoprotective agents, such as allopurinol, amifostine, denosumab, dexrazoxane, filgrastim, leucovorin, mesna, palifermin, pegfilgrastim, rasburicase, and sargramostim, together with one or more of the above mentioned active drugs, can be loaded into one drug delivery device. For example, the cytoprotective agent dexrazoxane can be loaded in the center of the multi-layered bioabsorbable fiber and the cytotoxic drug doxorubicin loaded in the outer layer of the fiber. Upon implanting a drug delivery device made from such a fiber, doxorubicin is released first to kill cancer cells and, after absorption of the outer fiber layer, dexrazoxane is then released. This results in limiting the amount of damage the doxorubicin can cause to nearby healthy tissues.

In some cases, it is desirable that the cytoprotective agent be released prior to the release of the cytotoxic agent. For example, leucovorin can be loaded in the outer layer of the bioabsorbable fiber, while methotrexate is included in the center of the fiber. A drug delivery device constructed using such a fiber will, upon implantation, release leucovorin first to protect normal cells in the bone marrow and digestive tract from damage that can be caused by methotrexate. The methotrexate is released after the outer fiber layer has been absorbed.

For some anti-cancer indications, a stent manufactured using the multi-layered bioabsorbable fibers described above, can be implanted in an artery that supplies blood to a cancerous tumor. More specifically, the stent can be implanted at a site proximal to the cancer. The implant site is not directly at the tumor's location, but nearby. The chemotherapy drug released from such a stent enters the circulation for a short time and then is taken up by cells in the tumor. This type of drug delivery is categorized as "local-systemic" drug delivery. For local-systemic drug delivery, the fibers can be advantageously loaded with a high drug dosage without a concomitant loss of mechanical strength. Typically, the drug weight is more than 10% of the stent weight.

A stent that includes the inventive drug-containing fibers is also capable of local drug delivery. For example, a stent can be implanted in a stenotic artery to restore blood flow and prevent cell proliferation that could lead to restenosis. Stents loaded with an anti-proliferative drug will fulfill the anti-stenosis mission. The amount of drug required for treating stenosis is significantly less than that required for cancer treatment. Typically the weight of incorporated drug is no more than 15% of the stent weight. The stent made from the inventive fibers is mechanically strong enough to keep the artery lumen open, yet will be absorbed soon enough to avoid long term issues such as stent-induced chronic foreign body reactions.

The use of stents via transcatheter intervention techniques has been generally successful for treating vessel narrowing/occlusion. This success has prompted the expansion of stent usage to peripheral arteries, urethra, trachea, esophagus, and the gastrointestinal tract to treat hypertrophic tissues and glands, tumors, and others diseases. The fibers described above can be used in the manufacture of drug delivery devices for these indications.

Without further elaboration, it is believed that the above description has adequately enabled the present invention. The following examples are, therefore, to be construed as merely illustrative, and not limitative of the remainder of the disclosure in any way whatsoever.

EXAMPLE 1

Drug-containing polymer fibers were prepared by dissolving 2.50 g of polycaprolactone, 2.50 g of sirolimus, and 0.125 g of lactic acid in 20 ml of methylene chloride. The solution was dispensed into a fiber-shaped mold and the methylene chloride evaporated to form a drug-containing bioabsorbable fiber precursor. Finally, the drug-containing bioabsorbable fiber precursor was drawn through a die at room temperature (20 to 25° C.) such that a bioabsorbable drug-containing fiber with a uniform diameter is formed.

EXAMPLE 2

Polymer films containing 0%, 2%, or 5% weak acid were prepared by dissolving 500 mg polycaprolactone with 0 mg, 10.5 mg, and 26.5 mg lactic acid, respectively, in 10 ml of a tetrahydrofuran/methylene chloride (1:9 ratio) solution. The resulting mixtures were poured into petri dishes, after which the dishes were placed in laminar flow hood until the solvent was completely evaporated to form a film. The resulting films were cut into 0.5 cm×0.5 cm samples. Triplicate samples of each film (a total of 15 samples) were each placed in a vial containing 25 ml phosphate-buffered saline (PBS) solution and incubated at 45° C. for a predetermined time points up to 4 weeks. At each time point, the 3 samples of each film in the vials were taken out for molecular weight measurement by gel permeation chromatography against a polystyrene standard. Following each molecular weight determination, the sample was returned to the vial after fresh PBS was added.

EXAMPLE 3

Polymer films containing 0%, 2%, or 5% weak base were prepared by dissolving 500 mg polycaprolactone, together with 0 mg, 10.5 mg, and 26.5 mg ammonium hydroxide, respectively, in 10 ml of a tetrahydrofuran/methylene chloride (1:9 ratio) solution. The resulting mixtures were poured into petri dishes, after which the dishes were placed in laminar flow hood until the solvent was completely evaporated to form a film. The resulting films were cut into 0.5 cm×0.5 cm samples. Triplicate samples of each film (a total of 15 samples) were each placed in a vial containing 25 ml PBS solution and incubated at 45° C. for a predetermined time points up to 4 weeks. At each time point, the 3 samples of each film in the vials were taken out for molecular weight measurement by gel permeation chromatography against a polystyrene standard. Following each molecular weight determination, the sample was returned to the vial after fresh PBS was added.

EXAMPLE 4

The tensile strength of bioabsorbable polylactide fibers was measured using a universal tensile tester with a load cell of 0.5 KN. After securing a fiber at each end using a clamp-type fixture, the fiber was pulled at a rate of 25 mm/min. The maximum load before fiber break was recorded. Tests were performed on polylactide fibers produced with and without the addition of 5% lactic acid.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of treating a disease caused by cell over-proliferation in a subject, the method comprising providing a bioabsorbable drug delivery device that includes a drug-containing bioabsorbable fiber and implanting the bioabsorbable drug delivery device into the subject in need of treatment, wherein the disease caused by cell over-proliferation is a tumor, the bioabsorable fiber is produced by the steps of dissolving both a bioabsorbable polymer and a first drug in an organic solvent to form a solution, dispensing the solution onto a flat surface, evaporating the organic solvent to form a sheet of drug-containing bioabsorbable polymer having at least two edges, adding a second drug to a surface of the sheet of drug-containing bioabsorbable polymer, joining the at least two edges to form a drug-containing bioabsorbable tube, sealing each end of the drug-containing bioabsorbable tube, and drawing the sealed drug-containing bioabsorbable tube through a die to form the drug-containing bioabsorbable fiber such that the drug-containing bioabsorbable fiber has a uniform diameter, the steps for producing the bioabsorable fiber are carried out at a temperature of 5° C. to 800° C. and the first drug is an anti-proliferative drug selected from the group consisting of fulvestrant, goserelin, histrelin, leuprolide, triptorelin, lenalidomide, biolimus, crizotinib, dasatinib, erlotinib, imatinib, lapatinib, pazopanib, pimecrolimus, sirolimus, sorafenib, sunitinib, tacrolimus, temsirolimus, vandetanib, zotarolimus, azacitidine, bendamustine, bleomycin, cabazitaxel, carboplatin, carmustine, cisplatin, cytarabine, dacarbazine, dactinomycin, daunorubicin, docetaxek doxorubicin, epirubicin, eribulin, etoposide, floxuridine, fludarabine, fluorouracil, gemcitabine, idarubicin, ifosfamide, irinotecan, ixabepilone, mechlorethamine, melphalan, methotrexate, mitoxantrone, nelarabine, oxaliplatin, paclitaxel, pemetrexed, pentostatin, pralatrexate, thiotepa, topotecan, vinblastine, clofarabine, decitabine, procarbazine, romidepsin, and streptozocin.

2. The method of claim 1, wherein the bioabsorbable polymer is selected from the group consisting of polycaprolactone, polydioxanone, polyglycolide, polylactides, poly-L-lactide, poly-D,L-lactide, poly (L-lactide-co-glycolide), poly (D,L-lactide-co-glycolide), poly (L-lactide-co-D,L-lactide), poly (L-lactide-co-trimethylene carbonate), polyhydroxyvalerate, and ethylvinylacetate.

3. The method of claim 1, wherein the bioabsorbable drug delivery device is implanted in a blood vessel, the gastrointestinal tract, or a duct.

4. The method of claim 3, wherein the second drug is a cytoprotective drug and the bioabsorbable drug delivery device is implanted in an artery that supplies blood to the tumor.

5. The method of claim 3, wherein the tumor is a gastrointestinal tumor or a gland tumor, the second drug is a cytoprotective drug, and the bioabsorbable drug delivery device is implanted in the gastrointestinal tract.

6. A method of treating a tumor in a subject, the method comprising the steps of forming a drug-containing bioabsorbable fiber by dissolving both a bioabsorbable polymer and a first drug in an organic solvent to form a solution, dispensing the solution onto a flat surface, evaporating the organic solvent to form a sheet of drug-containing bioabsorbable polymer having at least two edges, joining the at least two edges to form a drug-containing bioabsorbable tube, sealing each end of the drug-containing bioabsorbable tube, drawing the sealed drug-containing bioabsorbable tube through a die to form a drug-containing bioabsorbable fiber such that the drug-containing bioabsorbable fiber has a uniform diameter; and implanting the drug-containing bioabsorbable fiber into the subject in need of treatment, wherein the first drug is an anti-proliferative drug selected from the group consisting of fulvestrant, goserelin, histrelin, leuprolide, triptorelin, lenalidomide, biolimus, crizotinib, dasatinib, erlotinib, imatinib, lapatinib, pazopanib, pimecrolimus, sirolimus, sorafenib, sunitinib, tacrolimus, temsirolimus, vandetanib, zotarolimus, azacitidine, bendamustine, bleomycin, cabazitaxel, carboplatin, carmustine, cisplatin, cytarabine, dacarbazine, dactinomycin, daunorubicin, docetaxel, doxorubicin, epirubicin, eribulin, etoposide, floxuridine, fludarabine, fluorouracil, gemcitabine, idarubicin, ifosfamide, irinotecan, ixabepilone, mechlorethamine, melphalan, methotrexate, mitoxantrone, nelarabine, oxaliplatin, paclitaxel, pemetrexed, pentostatin, pralatrexate, thiotepa, topotecan, vinblastine, clofarabine, decitabine, procarbazine, romidepsin, and streptozocin.

7. The method of claim 6, further comprising adding a second drug to a surface of the sheet of drug-containing bioabsorbable polymer, wherein the second drug is a cytoprotective drug and the drug-containing bioabsorbable fiber is implanted in an artery that supplies blood to the tumor.

* * * * *